United States Patent [19]

Katakami et al.

[11] Patent Number: 4,539,151
[45] Date of Patent: Sep. 3, 1985

[54] BENZOTHIAZEPINE DERIVATIVES AND THEIR METHOD OF PREPARATION

[75] Inventors: Tsutomu Katakami; Nobuyuki Fukazawa, both of Yokohama; Hajime Iizuka, Hiratsuka, all of Japan

[73] Assignee: Mitsui Toatsu Chemicals, Inc., Tokyo, Japan

[21] Appl. No.: 625,815

[22] Filed: Jun. 28, 1984

[30] Foreign Application Priority Data

Jun. 29, 1983 [JP] Japan ................. 58-116179

[51] Int. Cl.$^3$ .......................................... C07D 281/02
[52] U.S. Cl. .............................................. 260/239.3 B
[58] Field of Search ............................. 260/239.3 B; 266/239.3 B

[56] References Cited

FOREIGN PATENT DOCUMENTS 2103614A 2/1983 United Kingdom ......... 260/239.3 B

Primary Examiner—Robert T. Bond
Attorney, Agent, or Firm—Fisher, Christen & Sabol

[57] ABSTRACT

This invention relates to benzothiazepine derivatives of the general formula

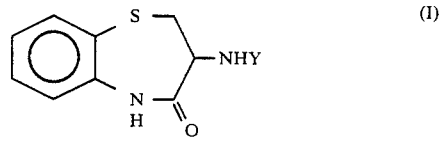

where Y is hydrogen, a $CHR_3$—$COOR_1$ group, an alkanoyl group or a —$COO(CH_2)_nR_4$ group where $R_1$ is hydrogen or a lower alkyl group, $R_3$ is hydrogen, an alkyl group, an alkylphenyl group or an aryl-lower alkyl group, $R_4$ is an aryl group and n is a whole number of 1 to 10, and to their method of preparation.

The benzothiazepine derivatives of this invention, including their salts, have an inhibitory effect on the angiotensin converting enzyme and are useful as raw materials or intermediates for the synthesis of antihypertensive agents and as intermediates for the manufacture of other drugs, agricultural chemicals and industrial chemicals.

4 Claims, No Drawings

BENZOTHIAZEPINE DERIVATIVES AND THEIR METHOD OF PREPARATION

BACKGROUND OF THE INVENTION (1.) Field of the Invention

This invention relates to novel benzothiazepine derivatives and their method of preparation.

(2.) Description of the Prior Art

It is generally known that angiotensin present in the blood acts on the smooth muscle of blood vessels to cause an intense contraction thereof and hence a marked rise in blood pressure. There are two forms of angiotensin: angiotensin I and angiotension II. Renin, which is secreated by the kidneys, acts on angiotensinogen to form angiotensin I. By the action of the angiotensin converting enzyme present in blood plasma and tissues, angiotensin I is converted into angiotensin II. It is angiotensin II that has biological activities.

A rise in blood pressure could be checked by inhibiting the angiotensin converting enzyme from acting on angiotensin I. With attention focused on this idea, the development of compounds which are useful as drugs for the treatment of hypertension and other cardiovascular diseases has hitherto been carried on.

However, there have been obtained neither compounds that are entirely satisfactory from the viewpoints of efficacy, side effects, toxicity and the like, nor intermediates that are useful in the synthesis of such compounds. Therefore, it would be still desirable to develop such compounds or intermediates.

Moreover, in applications where such compounds are used as raw materials or intermediates for the synthesis of drugs or as intermediates for the manufacture of agricultural chemicals and industrial chemicals, it is necessary that the desired compounds can be consistently produced in high yield and readily separated from by-products and the like.

SUMMARY OF THE INVENTION

It is an object of the present invention to provide novel compounds which have an inhibitory effect on the activity of angiotensin while exhibiting little toxicity.

It is another object of the present invention to provide novel compounds which are useful as intermediates for the manufacture of drugs (e.g., for the treatment of hypertension and other cardiovascular diseases), agricultural chemicals and industrial chemicals.

It is still another object of the present invention to provide a process for preparing such compounds.

According to the present invention, there are provided benzothiazepine derivatives of the general formula

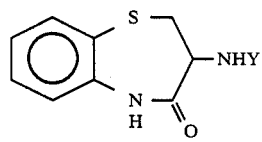

(I)

where Y is hydrogen, a —CHR$_3$—COOR$_1$ group, an alkanoyl group or a —COO(CH$_2$)$_n$R$_4$ group where R$_1$ is hydrogen or a lower alkyl group, R$_3$ is hydrogen, an alkyl group, an alkylphenyl group or an aryl-lower alkyl group, R$_4$ is an aryl group and n is a whole number of 1 to 10.

According to the present invention, there are also provided benzothiazepine derivatives of the general formula

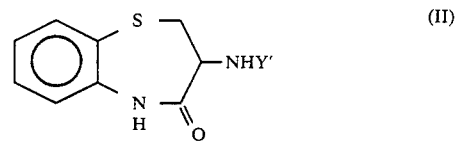

(II)

where Y' is hydrogen, an alkanoyl group or a benzyloxycarbonyl group.

DETAILED DESCRIPTION OF THE INVENTION

The benzothiazepine derivatives of the present invention will be more fully described hereinbelow.

In the general formulas (I) and (II), the lower alkyl group represented by R$_1$ is selected from the group consisting of methyl, ethyl, propyl, isopropyl, butyl, sec-butyl, t-butyl and the like. The alkanoyl group represented by Y or Y' is selected from the group consisting of formyl, acetyl, propanoyl, butanoyl, pivaloyl and the like. The alkyl group represented by R$_3$ is preferably a straight-chain or branched alkyl group having 1 to 10 carbon atoms, and specific examples thereof include methyl, ethyl, propyl, isopropyl, butyl, isobutyl, pentyl, hexyl, heptyl, octyl, nonyl, decyl and the like. In benzothiazepine derivatives as claimed in claim 5, a straight-chain or branched alkyl group having 5 to 10 carbon atoms is most preferably used as the alkyl group represented by R$_3$. The alkylphenyl group represented by R$_3$ has the formula

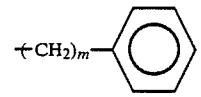

and, among such alkylphenyl groups, those in which m is 1 or 2 (i.e., benzyl and phenetyl) are particularly preferred. The aryl-lower alkyl group represented by R$_3$ is selected from the group consisting of tolylmethyl, tolylethyl, tolylpropyl, tolylbutyl, xylylmethyl, xylylethyl, xylylpropyl, xylylbutyl and the like. As the —COO(CH$_2$)$_n$R$_4$ group represented by Y, those in which n is a whole number of 1 to 5 are particularly preferred. Specific examples thereof include benzyloxycarbonyl, phenetyloxycarbonyl, phenylpropyloxycarbonyl, phenylbutyloxycarbonyl, phenylpentyloxycarbonyl, tolylmethoxycarbonyl, tolylethoxycarbonyl, tolylpropoxycarbonyl, tolylbutoxycarbonyl, tolylpentyloxycarbonyl, xylylmethoxycarbonyl, xylylethoxycarbonyl, xylylpropoxycarbonyl, xylylbutoxycarbonyl, xylylpentyloxycarbonyl and the like.

Typical benzothiazepine derivative falling within the scope of the present invention include: 3-amino-2,3-dihydro-1,5-benzothiazepin-4(5H)-one, 3-acetylamino-2,3-dihydro-1,5-benzothiazepin-4(5H)-one, 3-benzyloxycarbonylamino-2,3-dihydro-1,5-benzothiazepin-4(5H)-one and the like.

The compounds of the present invention can be prepared according to the following process.

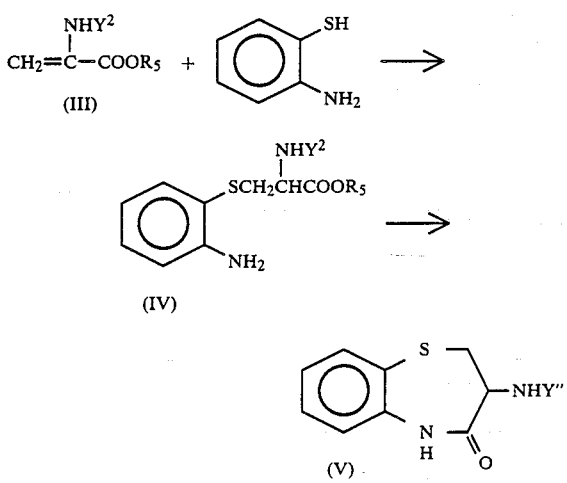

where $Y^2$ is an alkanoyl group, a $-COO(CH_2)_nR_4$ group where $R_4$ is an aryl group and n is a whole number of 1 to 10, or an ordinary amino-protecting group, $R_5$ is hydrogen or a lower alkyl group, and $Y''$ is hydrogen, an alkanoyl group, a $-COO(CH_2)_nR_4$ group where $R_4$ is an aryl group and n is a whole number of 1 to 10, or an ordinary amino-protecting group.

The term "ordinary amino-protecting group" as used herein comprehends urethane type protecting groups such as p-methoxybenzyloxycarbonyl, p-chlorobenzyloxycarbonyl, p-nitrobenzyloxycarbonyl, 3,5-dimethoxybenzyloxycarbonyl, 3,4,5-trimethoxybenzyloxycarbonyl, t-butoxycarbonyl and the like; and acyl type protecting groups such as trifluoroacetyl, trichloroacetyl, benzoyl and the like.

Specifically, a compound of the general formula (III) is reacted with 2-aminobenzenethiol at a temperature ranging from 0° C. to the boiling point of the reaction mixture, for a period of several hours. This reaction may be carried out in the absence of solvent or in the presence of a solvent selected from the group consisting of alcohols (such as methanol, ethanol, propanol and the like) and hydrocarbons (such as benzene, toluene, xylene and the like). Thus, there can preferably be obtained a compound of the general formula

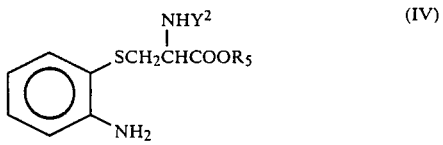

Then, the compound of the general formula (IV) can preferably be converted into a compound of the general formula (V), by heating the former alone or in a suitable solvent such as benzene, toluene, xylene, dimethylformamide, dimethyl sulfoxide, ethylene glycol, diphenyl ether or the like. The same purpose can be accomplished by using a dehydrating agent, such as dicyclohexylcarbodiimide or the like, suitable for cyclizing the compound of the general formula (IV) to form the compound of the general formula (V).

After the compound of the general formula (IV) has been cyclized, the alkanoyl, benzyloxycarbonyl or other amino-protecting group may be eliminated from the compound of the general formula (V), if desired, according to an ordinary procedure for the removal of protecting groups. Thus, there can be obtained a compound of the general formula (V) in which $Y''$ is hydrogen. For example, where $Y^2$ is benzyloxycarbonyl, this group can be removed by treating the compound with hydrogen bromide-acetic acid, hydrogen bromidetrifluoroacetic acid, hydrogen fluoride or the like, or by dissolving the compound in a suitable solvent such as ethanol, methanol, acetic acid or the like and hydrogenating it at a hydrogen pressure ranging from atmospheric pressure to 100 kg/cm², in the presence of a noble metal catalyst commonly used for hydrogenation, such as palladium-carbon, platinum-carbon, platinum oxide or the like.

If desired, the compound of the general formula (V) thus obtained may be combined with hydrochloric acid, hydrobromic acid and the like to form their salts.

The compound of the general formula (V) in accordance with the present invention contains two asymmetric carbon atoms in the molecule and, therefore, has various optical isomers. It is to be understood that all of such optical isomers fall within the scope of the present invention.

The benzothiazepine derivatives of the present invention, including their salts formed as above, have a powerful inhibitory effect on the angiotensin converting enzyme and are useful in the synthesis of drugs for the treatment of hypertension and other cardiovascular diseases. In addition, these compounds are also useful as intermediates for the synthesis of coronary dilators, psychotropic drugs and the like and as intermediates for the manufacture of agricultural chemicals and industrial chemicals.

The present invention is further illustrated by the following examples. However, these examples are not to be construed to limit the scope of the invention.

EXAMPLE 1

Preparation of N-acetyl-S-(2-aminophenyl)cysteine

A mixture consisting of 8.6 g of α-acetylaminoacrylic acid, 20 g of 2-aminobenzenethiol and 50 ml of ethanol was heated for an hour. After the ethanol was distilled off, ether was added to the residue so as to cause crystallization. Upon recrystallization from ethanol, there was obtained 8.9 g of the desired product. Its melting point (m.p.) was 143°–144° C.

EXAMPLE 2

Preparation of N-benzyloxycarbonyl-S-(2-aminophenyl)cysteine 23 g of α-benzyloxycarbonylaminoacrylic acid and 30 g of 2-aminobenzenethiol were dissolved in 20 ml of ethanol, and the resulting mixture was stirred at room temperature for an hour. After the solvent was distilled off, ether was added to the residue so as to cause crystallization. The precipitated crystals were separated by filtration and washed with ether to obtain 17.8 g of the desired compound. Its melting point was 150°–151° C.

EXAMPLE 3

Preparation of 3-acetylamino-2,3-dihydro-1,5-benzothiazepin-4(5H)-one 1.2 g of N-acetyl-S-(2-aminophenyl)cysteine was dissolved in 20 ml of xylene and the resulting solution was heated under reflux for 2 hours. After cooling, the precipitated crystals were separated and washed with methanol to obtain 0.8 g of the desired compound, or 3-acetylamino-2,3-dihydro-1,5-benzothiazepin-4(5H)-one. Its melting point was 283°–286° C.

EXAMPLE 4

Preparation of 3-benzyloxycarbonylamino-2,3-dihydro-1,5-benzothiazepin-4(5H)-one 17.8 g of N-benzyloxycarbonyl-S-(2-aminophenyl)-cysteine was dissolved in 250 ml of xylene and the resulting solution was heated under reflux for 4 hours. After the solvent was distilled off under reduced pressure, ether was added to the residue. The precipitated crystals were separated to obtain 12.1 g of the desired compound, or 3-benzyloxycarbonylamino-2,3-dihydro-1,5-benzothiazepin-4(5H)-one. Its melting point was 149°–151° C.

EXAMPLE 5

Preparation of 3-amino-2,3-dihydro-1,5-benzothiazepin-4(5H)-one 14 ml of a 25% solution of hydrogen bromide in acetic acid was added to 3.0 g of 3-benzyloxycarbonylamino-2,3-dihydro-1,5-benzothiazepin-4(5H)-one and the resulting mixture was stirred at room temperature for an hour. After the addition of ether, the precipitated crystals were separated by filtration to obtain 2.45 g of the hydrobroxide of the desired compound, or 3-amino-2,3-dihydro-1,5-benzothiazepin-4(5H)-one. Its melting point was 290° C. or above.

1.0 g of this hydrobromide was dissolved in water and the solution was alkalified by the addition of an aqueous solution of sodium carbonate. The precipitated crystals were separated by filtration to obtain 0.7 g of 3-amino-2,3-dihydro-1,5-benzothiazepin-4(5H)-one. When heated to determine its melting point, it decomposed at 182° C.

EXAMPLE 6

Preparation of 3-amino-2,3-dihydro-1,5-benzothiazepin-4(5H)-one 1.0 g of 3-benzyloxycarbonylamino-2,3-dihydro-1,5-benzothiazepin-4(5H)-one was dissolved in 20 ml of methanol and then hydrogenated at atmospheric pressure in the presence of 50 mg of 5% palladium-carbon. Thus, there was obtained the desired compound, or 3-amino-2,3-dihydro-1,5-benzothiazepin-4(5H)-one.

What is claimed is:

1. A benzothiazepine compound of the following formula

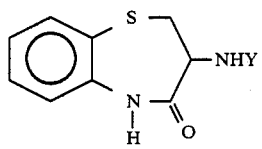

wherein Y is hydrogen, a CHR$_3$—COOR$_1$ group, an alkanoyl group having 1 to 5 carbon atoms or a —COO(CH$_2$)$_n$R$_4$ group wherein R$_1$ is hydrogen or a lower alkyl group having 1 to 4 carbon atoms, R$_3$ is hydrogen, an alkyl group having 1 to 10 carbon atoms, an aralkyl group being benzyl or phenethyl or an aryl-lower alkyl group where aryl is tolyl or xylyl and lower alkyl has 1 to 4 carbon atoms, R$_4$ is an aryl group being phenyl, tolyl or xylyl and n is a whole number of 1 to 10.

2. A benzothiazepine compound of the general formula

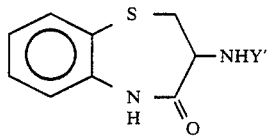

where Y' is hydrogen, an alkanoyl group having 1 to 5 carbon atoms or a benzyloxycarbonyl group.

3. A benzothiazepine compound as claimed in claim 1 which is 3-amino-2,3-dihydro-1,5-benzothiazepin-4(5H)-one, 3-acetylamino-2,3-dihydro-1,5-benzothiazepin-4(5H)-one or 3-benzyloxycarbonylamino-2,3-dihydro-1,5-benzothiazepin-4(5H)-one.

4. A process for preparing benzothiazepine compound of the following formula

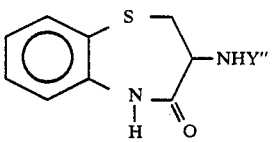

wherein Y'' is hydrogen, an acyl group being alkanoyl having 1 to 5 carbon atoms including trifluoroacetyl and trichloroacetyl or benzoyl, a —COO(CH$_2$)$_n$R$_4$ group where R$_4$ is an aryl group being phenyl, tolyl or xylyl and n is a whole number of 1 to 10, benzyloxycarbonyl group having a substitute or substitutes of P-methoxyl, P-chloro, P-nitro, 3,5-dimethoxy or 3,4,5-trimethoxy, or an alkoxycarbonyl group being t-butoxycarbonyl, which comprises reacting a compound of the following formula

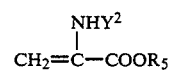

wherein Y$^2$ is the same is defined in Y''' except that hydrogen is excluded; with 2-aminobenzenethiol to form a compound of the following formula

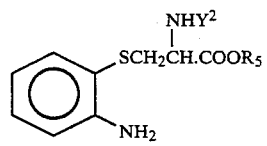

wherein Y$^2$ and R$_5$ is as previously defined; and then cyclizing the compound of the formula (IV) with or without subsequent elimination of the Y$^2$ group.

* * * * *